(12) United States Patent
DeBarber et al.

(10) Patent No.: US 8,158,435 B2
(45) Date of Patent: Apr. 17, 2012

(54) TANDEM MASS SPECTROMETRY FOR DETECTING AND/OR SCREENING FOR CONDITIONS ASSOCIATED WITH ALTERED STEROLS

(75) Inventors: Andrea DeBarber, Vancouver, WA (US); Robert D. Steiner, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 251 days.

(21) Appl. No.: 12/596,551

(22) PCT Filed: May 2, 2008

(86) PCT No.: PCT/US2008/062538
§ 371 (c)(1),
(2), (4) Date: Oct. 19, 2009

(87) PCT Pub. No.: WO2008/137767
PCT Pub. Date: Nov. 13, 2008

(65) Prior Publication Data
US 2010/0129923 A1    May 27, 2010

Related U.S. Application Data

(60) Provisional application No. 60/916,224, filed on May 4, 2007.

(51) Int. Cl.
*G01N 33/92* (2006.01)
*B01D 59/44* (2006.01)

(52) U.S. Cl. ............ 436/71; 436/63; 436/128; 436/131; 436/173; 435/11; 250/282

(58) Field of Classification Search ............. 436/63, 436/71, 128, 131, 173; 435/11; 250/281, 250/282
See application file for complete search history.

(56) References Cited

U.S. PATENT DOCUMENTS

| 5,629,210 | A | * | 5/1997 | Hercules et al. ............. 436/71 |
| 6,451,611 | B1 | | 9/2002 | Simonsen et al. |
| 6,673,555 | B1 | | 1/2004 | Grand-Perrett et al. |
| 7,192,779 | B1 | | 3/2007 | Shackleton |
| 7,473,560 | B2 | * | 1/2009 | Soldin ..................... 436/173 |
| 7,807,472 | B2 | * | 10/2010 | Xu et al. ..................... 436/87 |

FOREIGN PATENT DOCUMENTS

| JP | 11-56397 A | 3/1999 |
| KR | 10-0735831 B1 | 6/2007 |
| WO | WO0246772 A1 | 6/2002 |

OTHER PUBLICATIONS

Johnson. Rapid Communications in Mass Spectrometry, vol. 19, 2005, pp. 193-200.*
Johnson, D.W. et al., "A rapid screening procedure for cholesterol and dehydrocholesterol by electrospray ionization tandem mass spectrometry," Journal of Lipid Research, Oct. 2001, vol. 42, No. 10, pp. 1699-1705.
Griffiths, William J. et al., "Derivatisation for the characterisation of neutral oxosteroids by electrospray and matrix-assisted laser desorption/ionisation tandem mass spectrometry: the Girard P derivative," Rapid Communications in Mass Spectrometry, RCM 2003, vol. 17, No. 9, pp. 924-935.
Wang Yuqin et al., "Matrix-assisted laser desorption/ionization high-energy collision-induced dissociation of steroids: analysis of oxysterols in rat brain," Analytical Chemistry, Jan. 1, 2006, vol. 78, No. 1, pp. 164-173.
Griffiths, William J. et al., "Analysis of oxysterols by electrospray tandem mass spectrometry," Journal of the American Society for Mass Spectrometry, Mar. 2006, vol. 17, No. 3, pp. 341-362.
Johnson, David W., "A modified Girard derivatizing reagent for universal profiling and trace analysis of aldehydes and ketones by electrospray ionization tandem mass spectrometry," Rapid Communications in Mass Spectrometry, RCM 2007, vol. 21, No. 18, pp. 2926-2932.
Honda, Akira et al., "Highly sensitive quantification of 7alpha-hydroxy-4-cholesten-3-one in human serum by LC-ESI-MS/MS," Journal of Lipid Research, Feb. 2007, vol. 48, No. 2, pp. 458-464.
Chevy, F. et al., "Sterol profiling of amniotic fluid: a routine method for the detection of distal cholesterol synthesis deficit," Prenatal Diagnosis, Nov. 2005, vol. 25, No. 11, pp. 1000-1006.
Bove, Kevin E. et al., "Bile acid synthetic defects and liver disease: a comprehensive review," Pediatric and Developmental Pathology: The Official Journal of the Society for Pediatric Pathology and the Paediatric Pathology Society, Jul. 2004, vol. 7, No. 4, pp. 315-334.

* cited by examiner

*Primary Examiner* — Maureen Wallenhorst
(74) *Attorney, Agent, or Firm* — Schwabe, Williamson & Wyatt

(57) ABSTRACT

Embodiments of the present invention provide for detecting and/or screening for conditions associated with altered sterols by derivatization of sterols to provide suitable sensitivity and selectivity of detection using tandem mass spectrometry with electrospray ionization. Such testing may be performed to detect and/or screen for conditions such as Smith-Lemli-Opitz syndrome, familial hypercholesterolaemia, and cerebrotendinous xanthomatosis, or certain bile acid disorders.

23 Claims, 2 Drawing Sheets

TANDEM MASS SPECTROMETRY FOR DETECTING AND/OR SCREENING FOR CONDITIONS ASSOCIATED WITH ALTERED STEROLS

CROSS-REFERENCE TO RELATED APPLICATIONS

The present application claims priority to U.S. Provisional Patent Application No. 60/916,224, filed May 4, 2007, entitled "Tandem Mass Spectrometry for Newborn Screening of Conditions Associated with Altered Circulating Sterols," the entire disclosure of which is hereby incorporated by reference in its entirety.

TECHNICAL FIELD

Embodiments of the present invention relate to the field of newborn screening, and, more specifically, to methods of using tandem mass spectrometry for detecting and/or screening for conditions associated with altered sterols.

BACKGROUND

State newborn screening programs save thousands of lives as well as prevent serious morbidity, such as mental retardation, through the early detection and treatment of genetic conditions. Many more lives could be saved by expanding newborn screening to include additional disorders. Currently, newborn screening is not offered for disorders of sterol and bile acid metabolism.

Genetic alterations in sterol pathways result in the untimely mortality and morbidity caused by Smith-Lemli-Opitz syndrome (SLOS), familial hyper-cholesterolaemia (FH), cerebrotendinous xanthomatosis (CTX) and congenital adrenal hyperplasia (CAH). SLOS, FH and CAH were identified as conditions to consider for universal newborn screening in a recent American College of Medical Genetics report. Although CAH was a member of the screening panel ultimately recommended, SLOS and FH lacked a requisite criterion for inclusion; the availability of a suitable sensitive and selective screening test validated in a large population.

SLOS is an inborn error of cholesterol synthesis associated with cholesterol deficiency and involves accumulation of the cholesterol precursor 7-dehydrocholesterol and a derivative 8-dehydrocholesterol, as a result of reduced 7-dehydrocholesterol reductase activity. The incidence of SLOS is reported to be 1:20,000-40,000, but the carrier frequency may be as high as 1 in 30. Screening newborns for SLOS, in addition to enabling early institution of therapy, would allow genetic counseling. The "gold-standard" for confirmation of a SLOS diagnosis is gas chromatography (GC)-MS determination of the 7- and 8-dehydrocholesterol levels and their ratio to cholesterol in plasma.

FH is the most common serious genetic condition in the US, with a reported incidence as high as 1:500. FH has no phenotype at birth other than elevated plasma low density lipoprotein (LDL)-cholesterol due to various heterozygous defects in the LDL receptor gene or intracellular processing of the LDL-receptor complex. Although detection of elevated plasma LDL-cholesterol has been used in many studies as a surrogate for FH diagnosis, the "gold-standards" include either molecular genetic studies identifying a pathogenic mutation in the LDL-cholesterol receptor gene or biochemical studies showing defective LDL-cholesterol receptor activity in cultured fibroblasts. In the US population, the large number of identified mutations, along with assay expense and lack of general availability of both assays, makes identification via LDL-cholesterol mutation analysis or receptor activity impractical.

CTX is a rare genetic sterol condition caused by mutations in the CYP27A gene. The associated P450 enzyme is important in production of bile acids and when sterol 27-hydroxylase activity is blocked, substrates such as 7α-hydroxy-4-cholestene-3-one accumulate. CTX characteristically presents in childhood or adult life with symptoms caused by the accumulation in various tissues of cholesterol and cholestanol, formed in part from the elevated 7α-hydroxy-4-cholestene-3-one. Common CYP27A gene mutations have been identified with increased prevalence in several world populations and DNA screening has been suggested as a tool to enable diagnosis and genetic counseling in those countries.

CAH is the most common inborn error of the adrenal steroid pathways and is caused by mutations in the CYP21A2 gene in >90% of cases. The resulting steroid hormone imbalance, involving accumulation of the 21-hydroxylase substrate 17α-hydroxyprogesterone (17OHP), leads to salt-wasting crises in the newborn period. Pre-symptomatic diagnosis and hormone replacement therapy can be life-saving and screening for CAH by immunoassay measurement of 17OHP has been integrated into many newborn screening programs. One reason CAH screening has not been universal is the number of false positives associated with immunoassay 17OHP measurement.

Due to the impact of these conditions, there is still a need for a suitable sensitive and selective screening test for SLOS, FH, and CTX for early identification of the conditions. Such a screening test may also be applicable to other conditions, such as CAH. Similarly, screening may be used for various bile acid disorders exhibited in part by altered sterols in the body.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

μg/ml) and cholestanol from CTX-affected plasma was measured to range from 9.6-30 μg/ml (normal range positive diagnosis 13-150 μg/ml). The highest value obtained for any unaffected sample is indicated by a dashed line.

Figure 4:
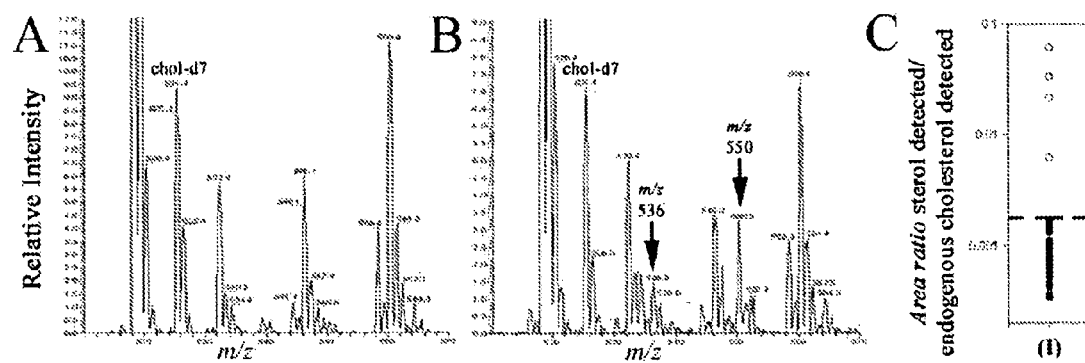

FIG. 4 illustrates neutral loss scans from unaffected (panel A) and CTX-affected (panel B) plasma. Spectra include any parent ion derivatives that lose neutral pyridine species of 79 Da. Detection of cholesterol-d, m/z 525 ion is indicated. The detection of other precursor species that may be found in affected samples is shown at m/z 536 and m/z 550. Comparison is shown (panel C) of free putative 7α-hydroxy-5β-cholestane-3-one ("I") at m/z 536 for unaffected (n=32, shaded circles) compared to untreated CTX-affected subjects (n=4, open circles). A logarithmic scale is used for area ratio values. The highest value obtained for any unaffected sample is indicated by dashed line.

DETAILED DESCRIPTION OF EMBODIMENTS OF THE INVENTION

In the following detailed description, reference is made to the accompanying drawings which form a part hereof, and in which are shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

For the purposes of the description, a phrase in the form "A/B" or in the form "A and/or B" means "(A), (B), or (A and B)". For the purposes of the description, a phrase in the form "at least one of A, B, and C" means "(A), (B), (C), (A and B), (A and C), (B and C), or (A, B and C)". For the purposes of the description, a phrase in the form "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In various embodiments of the present invention, methods, apparatuses, and systems for analyzing sterols and screening for conditions associated with altered sterols are provided. Such conditions include disorders of sterol and bile acid metabolism. In embodiments, exemplary conditions include Smith-Lemli-Opitz syndrome, familial hypercholesterolaemia, and cerebrotendinous xanthomatosis, as well as bile acid disorders, such as 3β-Δ5-C27-hydroxysteroid oxidoreductase deficiency and Δ4-3-oxosteroid-5β reductase deficiency.

Embodiments of the present invention provide for screening of conditions associated with altered sterols by derivatization of sterols to a GP-hydrazone to provide suitable sensitivity and selectivity of detection using tandem mass spectrometry with electrospray ionization. Thus, an embodiment of the present invention provides a method comprising providing a biological sample containing sterols, derivatizing the sterols by reacting the sterols with a derivatizing reagent, detecting the derivatized sterols using tandem mass spectrometry with electrospray ionization methodology amenable to high-throughput screening to quantify the sterols in the biological sample using deuterated internal standard or to determine a discriminatory metabolic sterol ratio, and comparing the quantified sterols or metabolic sterol ratio in the biological sample with values of sterols for unaffected individuals to determine whether the sterols in the biological sample are indicative of one or more condition associated with altered sterols.

In another embodiment, there is provided a method, comprising providing a biological sample containing sterols; derivatizing the sterols by reacting the sterols with a derivatizing reagent; detecting the derivatized sterols using tandem mass spectrometry with electrospray ionization to quantify the sterols in the biological sample or to determine a discriminatory metabolic sterol ratio; and comparing the quantified sterols or metabolic sterol ratio in the biological sample with values of sterols for unaffected individuals to determine whether the sterols in the biological sample are indicative of at least one of Smith-Lemli-Opitz syndrome, familial hypercholesterolaemia, cerebrotendinous xanthomatosis, 3β-Δ5-C27-hydroxysteroid oxidoreductase deficiency, and Δ4-3-oxosteroid-5β reductase deficiency.

For the purposes of describing embodiments of the present invention, the term "unaffected individuals" refers to those individuals that do not have the condition(s) associated with altered sterols. Such individuals may be used for comparative samples or controls.

Additional details regarding use of tandem mass spectrometry for screening may be found in U.S. Pat. No. 6,451,611, the entire contents of which are hereby incorporated by reference.

In an embodiment, tandem mass spectrometry with electrospray ionization (ESI-MS/MS) may be utilized to screen for various conditions associated with altered sterols. In an embodiment, ESI-MS/MS may be utilized to screen for SLOS, FH, and CTX with a single test.

In an embodiment, a suitable screen such as provided above may be utilized to screen for additional conditions, such as CAH, in the same test. Additional details regarding use of mass spectrometry for screening, in particular for screening of CAH, may be found in WO 0246772, the entire contents of which are hereby incorporated by reference.

ESI-MS/MS enables high throughput multi-analyte screening, and paves the way for expansion of newborn screening to include additional conditions detected by the same analytes or with the same test. ESI-MS/MS typically decreases false positives by improving method selectivity of detection schemes. However, the analysis of sterols by mass spectrometry is a challenge as sterols 1) are not efficiently ionized with ESI and 2) do not normally fragment under MS/MS conditions to produce a dominant product ion. Thus, embodiments of the present invention provide for derivatization of sterols to increase sensitivity and selectivity of detection using ESI-MS/MS.

Although the description primarily addresses the uses of embodiments of the present invention for newborn screening, methods of the present invention may be utilized for screening conditions in people of all ages, whether newborns, infants, toddlers, adults, etc. Embodiments of the present invention may be used to provide preliminary diagnoses of certain conditions, although typically a screen or preliminary diagnosis will be confirmed by diagnosis with other methods known in the art. Further, embodiments may be used to monitor the progression of a condition and/or the efficacy of a therapy being used to treat the condition.

In an embodiment, it has been shown that elevated blood sterols indicative of SLOS, FH and CTX may be detected with ESI-MS/MS methodology that may further be automated, in an embodiment, in a high throughput screening format, such as currently in use in newborn screening programs. If a suitable screening test, such as described herein, were provided for these conditions, such a test may be integrated into newborn screening programs and the burden of these disorders prevented or alleviated. In an embodiment, a further benefit is that CAH, routinely screened for by using immunoassay methodology, may also be detected in the same multiplex test that would identify SLOS, FH and CTX.

In an embodiment, the increase in sensitivity and selectivity afforded by derivatization may enable detection of the sterols indicative of SLOS, FH and CTX from filter paper blood spots or other sample types. In an embodiment, such derivatization may be sterol derivatization with Girard P reagent (1-(2-hydrazino-2-oxoethyl)pyridinium chloride) to Girard (G)P-hydrazone.

In an embodiment, there is provided an ESI-MS/MS method for the detection of sterols, such as dehydrocholesterol, cholesterol and cholestanol. In an embodiment, a method is provided for screening and/or predicting the occurrence of a condition associated with altered sterols in an individual, such as SLOS, FH, and/or CTX. In an embodiment, other such conditions include bile acid disorders, such as $3\beta$-$\Delta 5$-C27-hydroxysteroid oxidoreductase deficiency and $\Delta 4$-3-oxosteroid-$5\beta$ reductase deficiency.

For the purposes of describing embodiments of the present invention, the phrase "condition associated with altered sterols" refers to a condition in an individual associated with accumulation/elevation of sterols not seen in unaffected individuals caused, for example, by disruption of the sterol synthesis or processing pathways, including conditions such as SLOS, FH, and CTX, as well as certain bile acid disorders.

In an embodiment, derivatization may be effected with use of a derivatizing reagent, such as a Girard reagent. For the purposes of describing embodiments of the present invention, the term "Girard reagent" includes modified and unmodified Girard reagents, and includes Girard P, Girard T, and other such reagents. Additional reagents and details pertaining to use thereof may be found in Johnson, A Modified Girard Derivatizing Reagent for Universal Profiling and Trace Analysis of Aldehydes and Ketones by Electrospray Ionization Tandem Mass Spectrometry, Rapid Commun. Mass Spectrom., 21: 2926-2932 (2007), the entire contents of which are hereby incorporated by reference.

In an embodiment, derivatization of sterols with GP-reagent forms molecules with a quaternary nitrogen cation (FIG. 1, panel A) that may be readily analyzed with ESI and may fragment to provide a dominant product ion from the neutral loss of 79 Da (pyridine). In an embodiment, the neutral loss from the GP-derivative is potentially more selective than that from a GT-derivative (neutral loss of trimethylamine from palmitoylcarnitine produces the same ion as for androstenedione). However, in an embodiment, GT-derivatization using Girard T reagent ((carboxymethyl)trimethyl-ammonium chloride) may be used instead of GP-derivatization.

Figure 1:
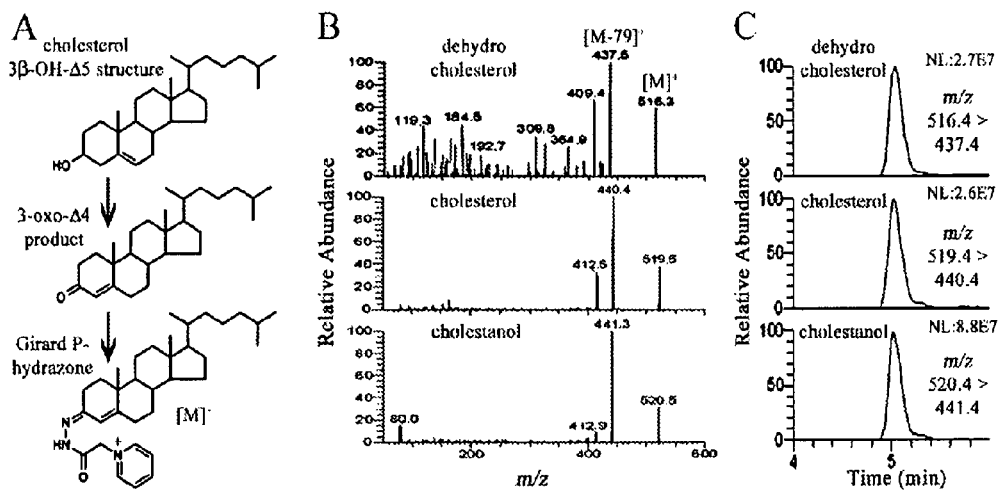
FIG. 1 (panels A, B, and C) illustrate cholesterol conversion to a 3-oxo-Δ4 product capable of forming a GP-hydrazone, for analysis with positive mode electrospray ionization (panel A). Each derivative fragments with tandem mass spectrometry to give a dominant product ion $[M-79]^+$ from the neutral loss of pyridine (panel B). Sterols are readily detected after treatment with cholesterol oxidase from *Nocardia*; cholesterol at 100 μg/ml plasma (10 ng on-column sensitivity), cholestanol at 50 μg/ml and dehydrocholesterol at 100 μg/ml (panel C).

In an embodiment, GP-derivatization for each sterol gave a dominant 79 Da neutral loss product ion from a strong molecular ion (FIG. 1, panel B). Instrument conditions were optimized for sensitivity and selectivity using infusion experiments to examine analyte ionization and fragmentation. Cholesterol, dehydrocholesterol and cholestanol detected by monitoring the transition from precursor derivative ion to product ion (FIG. 1, panel C) demonstrated linearity at molar ratios between 0 and 20 relative to deuterated cholesterol internal standard ($R^2$ values>0.95). Cholesterol-d, was added to plasma at a concentration of 25 µg/ml. In embodiments, samples were subjected to alkaline hydrolysis for one hour or free sterols were directly isolated by liquid-liquid extraction with hexane. In an embodiment, after evaporation of hexane under nitrogen, incubation for one hour with pH7 buffered aqueous cholesterol oxidase (from *Streptomyces* or *Nocardia*) converted the $3\beta$-hydroxy-$\Delta 5$ structure of cholesterol and analogues to 3-oxo-$\Delta 4$ products then extracted with diethyl ether:hexane (9:1). The solvent was evaporated and treated for 10 minutes with methanolic 10 mmol/L GP-reagent solution with 1% acetic acid which converted the sterol 3-oxo group to a hydrazone.

In an embodiment, analytes were detected with a TSQ Quantum Discovery triple-stage MS (ThermoElectron) housed in the BioAnalytical Shared Resource (BSR), with an in-line SCX cation exchange guard column (ThermoHypersil) to remove excess GP reagent. Sterol derivatives were eluted using 20 mM ammonium formate in 80% methanol. Multiple reaction monitoring transitions were m/z 516>437 for dehydrocholesterol, m/z 518>439 or 519>440 for cholesterol, m/z 520>441 for cholestanol, and m/z 525>446 for cholesterol-d, internal standard. Monitoring of the transition m/z 519>440 (for naturally occurring cholesterol-$C_{13}$ isomer) was found to decrease method variability from detector saturation. The symbol "m/z" refers to a mass-to-charge ratio.

In accordance with an embodiment, the increase in sensitivity and selectivity afforded by GP-derivatization enabled the detection (at molar ratios of ~10:1 to cholesterol-$d_7$) of free cholesterol extracted from 10 µl plasma (replicate analysis n=3) with an inter-assay variation of 15% RSD. Free dehydrocholesterol was detected (at molar ratios of ~2:1 to cholesterol-$d_7$) from 10 µl plasma (n=3) with an intra-assay variation of 22% RSD. Although, in an embodiment, excess derivatization reagent may be removed with an SCX guard, sterols are generally not separated prior to analysis so detection is typically for the sum of dehydrocholesterol isomers. Free cholestanol was detected (at molar ratios of ~2:1 to cholesterol-$d_7$) from 10 µl plasma (n=3) with an inter-assay variation of 6% RSD.

For free sterols, the dehydrocholesterol to cholesterol ratios for SLOS plasma samples ranged from 4 to 7 times the highest control sample ratio in multiple experiments. For free sterols, the cholestanol to cholesterol ratios for a CTX sample ranged from 4 to 10 times the highest control sample ratio in multiple experiments.

Figure 2:
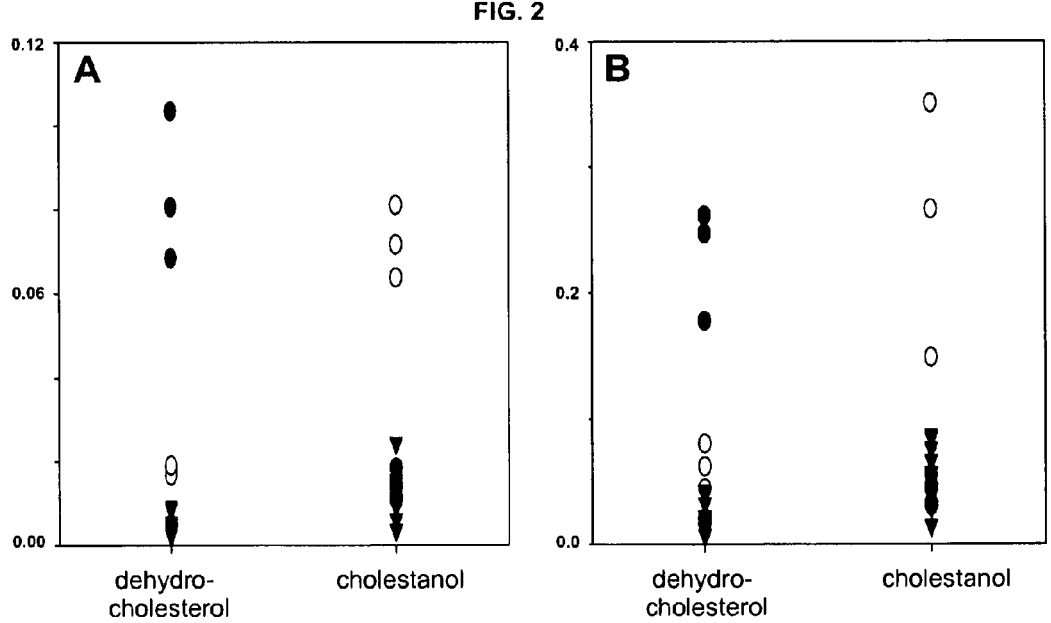
FIG. 2 illustrates plasma levels of sterols in controls (triangles) and affected patients (SLOS shaded circles, CTX open circles). In panel A the sterol/cholesterol area ratio is plotted, and in panel B the sterol/cholesterol-$d_7$ area ratio is plotted. Increases are detected in SLOS and CTX patients.

Data resulting from ESI-MS/MS may be utilized in a variety of forms, including quantifying sterols in a biological sample using deuterated internal standard or determining a discriminatory metabolic sterol ratio. FIG. 2 illustrates plasma levels of sterols in controls (triangles) and affected patients (SLOS shaded circles, CTX open circles). In panel A the sterol/cholesterol area ratio is plotted, and in panel B the sterol/cholesterol-$d_7$ area ratio is plotted. As shown, increases are detected in SLOS and CTX patients.

Figure 3:
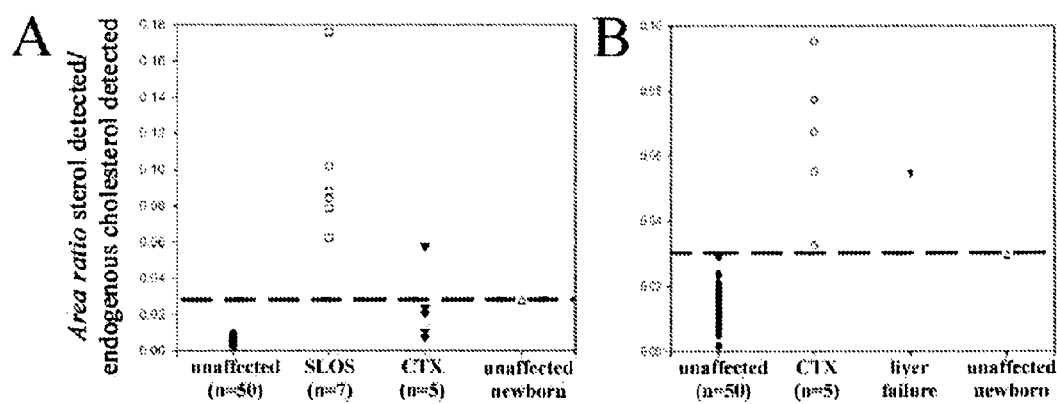
FIG. 3 illustrates a comparison of area ratio values for plasma free dehydrocholesterol divided by cholesterol signal (panel A) for unaffected, SLOS-affected, CTX-affected, and unaffected newborn subjects. Also a comparison of area ratio values for free cholestanol divided by cholesterol signal (panel B) for unaffected, CTX-affected, and unaffected newborn subjects. A liver failure patient was also discriminated. The concentration of 7-dehydrocholesterol from SLOS-affected plasma was previously measured by GC-MS to be 4 μg/ml and greater (normal range positive diagnosis 5-524

In an embodiment, to decrease method variation, the ratio of dehydrocholesterol or cholestanol signal to the endogenous cholesterol signal detected may be used. From CTX-patient plasma, an endogenous metabolite area ratio value for free cholestanol to cholesterol was detected with an intra-assay variation of 30% RSD (n=3) at >1.6-fold the highest control sample value. Use of endogenous metabolite area ratios enabled discrimination between plasma from SLOS and CTX-affected patients and control plasma (see FIG. 3).

In addition to characterizing the Girard-P derivatives of dehydrocholesterol, cholesterol and cholestanol, in accordance with embodiments of the present invention, novel disorder-associated Girard-P derivative ions utilizing MS/MS neutral loss scanning have been identified. With CTX, for example, precursor ions that lost a neutral 79 Da species were clearly detected from untreated CTX-affected patient plasma (n=4) and were not detected from unaffected controls (FIG. 4, comparison of unaffected (panel A) versus CTX-affected (panel B)). One example is the m/z 550 ion; a putative derivative of 7a,12a-dihydroxy-4-cholestene-3-one.

Another example is the m/z 536.3 ion (also referred to simply as an m/z 536 ion); a putative Girard-P derivative of 7α-hydroxy-5β-cholestane-3-one that may also be detected without cholesterol oxidase conversion. In an embodiment, detection of this candidate biomarker by monitoring the transition from m/z 536.3 precursor to $[M-79]^+$ product ion allowed calculation of area ratio values for free 7α-hydroxy-5β-cholestane-3-one signal divided by free cholesterol signal detected. Replicate area ratio values were obtained for a CTX-affected sample (at >13-fold the highest unaffected sample) with an intra-assay variation of 11% RSD. The lowest area ratio value obtained for a CTX-affected sample was >4-fold the highest unaffected value (see FIG. 4, panel C). Although the bile acid precursor 7α-hydroxy-5β-cholestane-3-one has been detected in hepatic microsomes from CTX-affected patients, it was not detectable under conditions previously used to examine bile alcohols present in plasma. Novel signature molecules like 7α-hydroxy-5β-cholestane-3-one detected using HT ESI-MS/MS methodology will be valuable for population-based screening.

Similar to the results shown in FIG. 4, panel A and B, a 3β-Δ5-C27-hydroxysteroid oxidoreductase deficiency would exhibit elevated m/z 550 ion and m/z 536 ion. 3β-hydroxy-Δ5 bile alcohols replace normal 5β-saturated bile alcohols and acids. In an embodiment, 3β-hydroxy-Δ5 bile alcohols may be converted to 3-keto-Δ4 with cholesterol oxidase, derivatized and detected using methodology described herein. The presence of 3β,7α-dihydroxy-, and 3β,7α,12α-trihydroxy-Δ5-bile acids and alcohols are shown in affected patients, see Fischler, et al., Cholestatic liver disease in adults may be due to an inherited defect in bile acid biosynthesis, Journal of Internal Medicine, 262, 254-262 (2007), the entire contents of which are hereby incorporated by reference.

Complete absence of chenodeoxycholic and cholic acid was demonstrated in a child affected from Δ4-3-oxosteroid-5β reductase deficiency, see Palermo et al., Human $Δ^4$-3-oxosteroid 5β reductase (AKR1D1) deficiency and steroid metabolism, Steroids, 73, 417-423 (2008), the entire contents of which are hereby incorporated by reference. As such, in an embodiment, in a patient suffering from a Δ4-3-oxosteroid-5β reductase deficiency, one may be able to detect elevated m/z 550 ion as a biomarker of the disorder.

Newborn screening generally uses analyte extraction from 3.2 mm or 4.8 mm disks punched from dried blood spots on filter-paper, equivalent to around 3.4 μl and 7.6 μl of blood respectively. Although the data above is for 10 μl plasma, the methodology may also be utilized for sterol detection from neonatal blood spots as well.

Embodiments of the present invention provide sensitive and selective high throughput multi-analyte detection which may be integrated into MS/MS platforms commonly found in newborn screening, or may be utilized as a separate testing or screening platform. Testing or screening may be performed to determine or to assist in determining an initial presence of, or a diagnosis of, one or more condition. In an alternative embodiment, embodiments may be used to track the progress of certain conditions and/or treatments by conducting multiple tests over a period of time (weeks, months, years) to track the sterol levels and the impact of time and/or various treatments. In addition, an embodiment of the invention may be used to conduct large-scale screening of cholesterol levels in individuals.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A method of diagnosing or screening an individual for conditions associated with altered sterols, comprising:
   providing a biological sample containing sterols, the sample obtained from the individual;
   derivatizing the sterols by reacting the sterols with a derivatizing reagent;
   detecting the derivatized sterols using tandem mass spectrometry with electrospray ionization amenable to high-throughput screening to quantify the sterols in the biological sample using deuterated internal standard or to determine a discriminatory metabolic sterol ratio; and
   comparing the quantified sterols or metabolic sterol ratio in the biological sample with values of sterols for individuals unaffected with a condition associated with altered sterols to determine whether the sterols in the biological sample are elevated compared to the values of sterols for the individuals unaffected and thus indicative of one or more conditions associated with altered sterols,
   wherein the conditions associated with altered sterols comprise Smith-Lemli-Opitz syndrome, familial hypercholesterolaemia, and cerebrotendinous xanthomatosis, and
   wherein the comparing comprises comparing data for the quantified sterols or metabolic sterol ratio in the sample with values of sterols for the unaffected individuals to determine whether the quantified sterols or metabolic sterol ratio in the sample are indicative independently of each of the conditions associated with altered sterols.

2. The method of claim 1, wherein the sterols comprise at least one of dehydrocholesterol, cholesterol, and cholestanol.

3. The method of claim 1, wherein the biological sample comprises blood.

4. The method of claim 1, wherein the biological sample comprises plasma.

5. The method of claim 1, wherein detecting the derivatized sterols using tandem mass spectrometry with electrospray ionization methodology amenable to high-throughput screening to quantify the sterols in the biological sample using deuterated internal standard or to determine a discriminatory metabolic sterol ratio comprises quantifying presence of 7α-hydroxy-5β-cholestane-3-one and/or 7a,12a-dihydroxy-4-cholestene-3-one.

6. The method of claim 1, wherein detecting the derivatized sterols using tandem mass spectrometry with electrospray ionization methodology amenable to high-throughput screening to quantify the sterols in the biological sample using deuterated internal standard or to determine a discriminatory metabolic sterol ratio comprises identifying sterol Girard derivatives indicative of one or more condition by loss of a neutral 79 Da species.

7. The method of claim 6, wherein the sterol Girard derivatives are at least one ion selected from an m/z 536 ion and an m/z 550 ion.

8. The method of claim 1, wherein the derivatizing reagent is a Girard reagent.

9. The method of claim 1, wherein the derivatizing reagent is Girard T reagent.

10. The method of claim 1, wherein the derivatizing reagent is Girard P reagent.

11. A method of diagnosing or screening an individual for one or more condition associated with altered sterols, comprising:
provinding a biological sample containing sterols, the sample obtained from the individual;
derivatizing the sterols by reacting the sterols with a derivatizing reagent;
detecting the derivatized sterols using tandem mass spectrometry with electrospray ionization to quantify the sterols in the biological sample or to determine a discriminatory metabolic sterol ratio; and
comparing the quantified sterols or metabolic sterol ratio in the biological sample with values of sterols for individuals unaffected with a condition associated with altered sterols to determine whether the sterols in the biological sample are elevated compared to the values of sterols for the individuals unaffected and thus indicative independently of each of Smith-Lemli-Opitz syndrome, familial hypercholesterolaemia, cerebrotendinous xanthomatosis, 3β-Δ5-C27-hydroxysteroid oxidoreductase deficiency, and Δ4-3-oxosteroid-5β reductase deficiency.

12. The method of claim 11, wherein the derivatizing reagent is a Girard reagent.

13. The method of claim 11, wherein the derivatizing reagent is Girard T reagent.

14. The method of claim 11, wherein the derivatizing reagent is Girard P reagent.

15. The method of claim 11, wherein the sterols comprise at least one of dehydrocholesterol, cholesterol, and cholestanol.

16. The method of claim 11, wherein detecting the derivatized sterols using tandem mass spectrometry with electrospray ionization to quantify the sterols in the biological sample or to determine a discriminatory metabolic sterol ratio comprises identifying sterol Girard derivatives by loss of a neutral 79 Da species indicative of at least one of Smith-Lemli-Opitz syndrome, familial hypercholesterolaemia, cerebrotendinous xanthomatosis, 3β-Δ5-C27-hydroxysteroid oxidoreductase deficiency, and Δ4-3-oxosteroid-5β reductase deficiency.

17. A method of diagnosing or screening an individual for one or more condition associated with altered sterols, comprising:
providing a biological sample containing sterols, the sample obtained from the individual;
derivatizing the sterols by reacting the sterols with a derivatizing reagent;
detecting the derivatized sterols using tandem mass spectrometry with electrospray ionization amenable to high-throughput screening to quantify the sterols in the biological sample using deuterated internal standard or to determine a discriminatory metabolic sterol ratio; and
comparing the quantified sterols or metabolic sterol ratio in the biological sample with values of sterols for individuals unaffected with a condition associated with altered sterols to determine whether the sterols in the biological sample are elevated compared to the values of sterols for the individuals unaffected and thus indicative of the one or more condition associated with altered sterols, wherein the one or more condition associated with altered sterols comprises a bile acid disorder.

18. The method of claim 17, wherein the bile acid disorder comprises at least one of 3β-Δ5-C27-hydroxysteroid oxidoreductase deficiency and Δ4-3-oxosteroid-5β reductase deficiency.

19. A method of diagnosing or screening an individual for one or more condition associated with altered sterols, comprising:
providing a biological sample containing sterols, the sample obtained from the individual;
derivatizing the sterols by reacting the sterols with a derivatizing reagent;
detecting the derivatized sterols using tandem mass spectrometry with electrospray ionization amenable to high-throughput screening to quantify the sterols in the biological sample using deuterated internal standard or to determine a discriminatory metabolic sterol ratio, wherein detecting the derivatized sterols comprises quantifying presence of 7α-hydroxy-5β-cholestane-3-one and/or 7a,12a-dihydroxy-4-cholestene-3-one; and
comparing the quantified sterols or metabolic sterol ratio in the biological sample with values of sterols for individuals unaffected with a condition associated with altered sterols to determine whether the sterols in the biological sample are elevated compared to the values of sterols for the individuals unaffected and thus indicative of the one or more condition associated with altered sterols.

20. A method of diagnosing or screening an individual for one or more condition associated with altered sterols, comprising:
providing a biological sample containing sterols, the sample obtained from the individual;
derivatizing the sterols by reacting the sterols with a derivatizing reagent;
detecting the derivatized sterols using tandem mass spectrometry with electrospray ionization amenable to high-throughput screening to quantify the sterols in the biological sample using deuterated internal standard or to determine a discriminatory metabolic sterol ratio, wherein detecting the derivatized sterols comprises identifying sterol Girard derivatives indicative of one or more condition by loss of a neutral 79 Da species; and
comparing the quantified sterols or metabolic sterol ratio in the biological sample with values of sterols for individuals unaffected with a condition associated with altered sterols to determine whether the sterols in the biological sample are elevated compared to the values of sterols for the individuals unaffected and thus indicative of the one or more condition associated with altered sterols.

21. The method of claim 20, wherein the sterol Girard derivatives are at least one ion selected from an m/z 536 ion and an m/z 550 ion.

22. A method of diagnosing or screening an individual for one or more condition associated with altered sterols, comprising:
providing a biological sample containing sterols, the sample obtained from the individual;
derivatizing the sterols by reacting the sterols with a derivatizing reagent;

detecting the derivatized sterols using tandem mass spectrometry with electrospray ionization to quantify the sterols in the biological sample or to determine a discriminatory metabolic sterol ratio;

comparing the quantified sterols or metabolic sterol ratio in the biological sample with values of sterols for individuals unaffected with a condition associated with altered sterols to determine whether the sterols in the biological sample are elevated compared to the values of sterols for the individuals unaffected and thus indicative of at least one of Smith-Lemli-Opitz syndrome, familial hypercholesterolaemia, cerebrotendinous xanthomatosis, 3β-Δ5-C27-hydroxysteroid oxidoreductase deficiency, and Δ4-3-oxosteroid-5β reductase deficiency; and comparing the quantified sterols or metabolic sterol ratio in the biological sample with values of sterols for individuals unaffected with a condition associated with altered sterols to determine whether the sterols in the biological sample are elevated compared to the values of sterols for the individuals unaffected and thus indicative of congenital adrenal hyperplasia.

23. A method of diagnosing or screening an individual for one or more condition associated with altered sterols, comprising:

providing a biological sample containing sterols, the sample obtained from the individual;

derivatizing the sterols by reacting the sterols with a derivatizing reagent;

detecting the derivatized sterols using tandem mass spectrometry with electrospray ionization to quantify the sterols in the biological sample or to determine a discriminatory metabolic sterol ratio, wherein detecting the derivatized sterols comprises identifying sterol Girard derivatives by loss of a neutral 79 Da species; and comparing the quantified sterols or metabolic sterol ratio in the biological sample with values of sterols for individuals unaffected with a condition associated with altered sterols to determine whether the sterols in the biological sample are elevated compared to the values of sterols for the individuals unaffected and thus indicative of at least one of Smith-Lemli-Opitz syndrome, familial hypercholesterolaemia, cerebrotendinous xanthomatosis, 3β-Δ5-C27-hydroxysteroid oxidoreductase deficiency, and Δ4-3-oxosteroid-5β reductase deficiency.

\* \* \* \* \*